United States Patent
Dittrich et al.

(10) Patent No.: US 10,101,085 B2
(45) Date of Patent: Oct. 16, 2018

(54) DIRECTIONAL FREEZING

(71) Applicant: Roche Diagnostics Operations, Inc., Indianapolis, IN (US)

(72) Inventors: Juergen Dittrich, Habach (DE); Guenter Ziegler, Polling (DE)

(73) Assignee: Roche Diagnostrics Operations, Inc., Indianapolis, IN (US)

( * ) Notice: Subject to any disclaimer, the term of this patent is extended or adjusted under 35 U.S.C. 154(b) by 718 days.

(21) Appl. No.: 14/605,107

(22) Filed: Jan. 26, 2015

(65) Prior Publication Data

US 2015/0128445 A1  May 14, 2015

Related U.S. Application Data

(63) Continuation of application No. PCT/EP2013/065604, filed on Jul. 24, 2013.

(30) Foreign Application Priority Data

Jul. 26, 2012  (EP) .................................... 12178024

(51) Int. Cl.
  *F26B 5/06* (2006.01)
  *A61K 9/19* (2006.01)
  *F25C 1/10* (2006.01)
  *F25C 1/16* (2006.01)

(52) U.S. Cl.
  CPC .................. *F26B 5/06* (2013.01); *A61K 9/19* (2013.01); *F25C 1/10* (2013.01); *F25C 1/16* (2013.01)

(58) Field of Classification Search
  CPC .. F26B 5/06; F26B 5/04; F26B 11/049; F26B 17/128; F25D 3/00; F25D 3/10; F25D 31/00; F25D 2400/30; A01N 1/02; A61K 9/19

USPC ..................................... 34/92, 361, 284–298
See application file for complete search history.

(56) References Cited

U.S. PATENT DOCUMENTS

| 3,537,189 | A | | 11/1970 | Bender et al. |
| 4,531,373 | A | | 7/1985 | Rubinsky |
| 5,873,254 | A | * | 2/1999 | Arav ........................ A01N 1/02 62/374 |

(Continued)

FOREIGN PATENT DOCUMENTS

| EP | 0848221 A1 | 6/1998 |
| EP | 2476978 A1 | 7/2012 |
| WO | 2011/098996 A2 | 8/2011 |

OTHER PUBLICATIONS

International Search Report dated Aug. 26, 2013 in Application No. PCT/EP2013/065604, 5 pages.

(Continued)

*Primary Examiner* — John McCormack
(74) *Attorney, Agent, or Firm* — Roche Diagnostrics Operations, Inc.

(57) ABSTRACT

The invention relates to an apparatus and a method of freezing a liquid substance contained in at least one receptacle, comprising the steps of: providing the liquid substance in at least one receptacle, providing a cooling chamber and a cooling device having a cooling surface; setting the temperature of the cooling surface, starting a freezing procedure by placing the receptacle with the liquid substance therein on the cooling surface to form a seed or initial zone of nucleation; and continuing the freezing procedure to completely freeze the substance.

16 Claims, 5 Drawing Sheets

(56) References Cited

U.S. PATENT DOCUMENTS

| | | | |
|---|---|---|---|
| 5,964,043 A * | 10/1999 | Oughton | F26B 5/06 |
| | | | 34/284 |
| 2007/0022622 A1 | 2/2007 | Lanaway et al. | |
| 2012/0159803 A1 * | 6/2012 | Van Veen | F26B 5/06 |
| | | | 34/284 |

OTHER PUBLICATIONS

Constantino and Pikal, "The Role of Water in Physical Transformations in Freeze-dried Products," Freeze Drying, 2002, p. 247.
Patapoff, Thomas W. and Overcashier, David E., "The Importance of Freezing on Lyophilization Cycle Development," BioPharm, 2002, pp. 16-21.
Searles, James A. et al., "The Ice Nucleation Temperature Determines the Primary Drying Rate of Lyophilization for Samples Frozen on a Temperature-Controlled Shelf," Journal of Pharmaceutical Sciences, 2001, pp. 860-871, vol. 90, No. 7.

\* cited by examiner

Fig. 6

DIRECTIONAL FREEZING

CROSS-REFERENCE TO RELATED APPLICATIONS

This application is a continuation of PCT/EP2013/065604 filed Jul. 24, 2013 and claims priority to EP Patent Application No. 12178024.1 filed Jul. 26, 2012, the disclosures of which are hereby incorporated by reference in their entirety.

FIELD OF THE INVENTION

The present invention relates to a method and apparatus for the freezing of liquid substances contained in at least one receptacle, wherein a cooling surface is adapted to make surface contact with the receptacle and thereby to have a portion of the liquid substance form a seed or zone of nucleation or initial solidification. The invention further refers to a method and an apparatus for freeze-drying by the use of the freezing procedure according to the present invention. In methods and apparatuses according to the present invention, preconditions of freezing are applied to obtain optimal crystallization structures in the freezing process with regard to sublimation efficiency in a freeze-drying procedure.

BACKGROUND

Freeze-drying is the sublimation of a frozen, aqueous solution, usually at moderate temperatures and decreased pressure for water-based solutions and has been used in many areas, including the food industry and pharmacology, and also has some history in materials research. In particular, freeze-drying has been used for conserving reagents in the field of diagnostics such as clinical chemistry or immuno-diagnostics, and is particularly useful for long-term conservation of unstable fluid reagents like, for example, reference reagents, controls or calibrators for use in clinical chemistry analyzers or immunological analyzers such as protein solutions, human or animal blood sera.

Thus, the process of freeze-drying (also called lyophilization process) consists of the step of freezing the aqueous solution and the subsequent step of sublimating the frozen substance (ice crystals) in a drying process. Most of the conventional freeze-drying systems consist of equipment performing both the steps of freezing and drying in a single chamber, mainly because of cost reasons. As the freezing process in such a single chamber takes a relative long time, instable product may be shock-frozen in front of the drying/sublimation process. However, since these systems typically perform freeze-drying simultaneously on a plurality of receptacles, e.g. hundreds or even in large scale production up to 100.000 receptacles collected in, for example, a batch, such single chamber solutions have the inherent disadvantage that a high number of receptacles must be sequentially filled and added to the batch before the transfer into the freeze-dryer chamber can follow. Consequently, during the filling of the batch, a large number of filled receptacles must wait at ambient conditions until all receptacles of a batch for lyophilization have been filled, before the transfer into the chamber may be performed. During this storage, the filled receptacles, waiting in the batch, may suffer due to their instability in liquid state.

A remedy to this problem is to reduce the waiting time of the filled receptacles by having the freezing of the aqueous solution take place in a separate freezer, i.e. independently from the drying of the frozen solution. By this way, the aqueous solution, e. g. of reagents, can immediately after the respective receptacle has been filled be frozen sequentially or block-wise, e.g. using trays, and are then collected in a batch as frozen substance receptacles. Consequently, the frozen substance receptacles are not subject to deteriorating effects and can be effectively stored during the batch filling process in a frozen condition, e. g. for many hours or even longer. When the batch has been filled, a batch-wise sublimation is performed in a dryer, representing a separate entity from the freezer, without requiring that the freezing process must be stalled while preparing the next batch of frozen substance receptacles.

Conventionally, the freezing of the receptacles is performed batch-wise in a freeze dryer, by arranging the respective receptacles on pre-cooled shelfs inside the freeze dryer chamber. This has the above discussed disadvantage of deteriorating effects taking place while the batches are being prepared prior to freezing, and a number of such cooling chambers may need to be operated in parallel to avoid the deteriorating effects.

Moreover, the transport of batches into the chamber requires the chamber to be opened to replace batches for freezing. In this transition, because a large number of receptacles, with the internally product at room temperature (RT), carry a significant amount of heat into the chamber and the temperature distribution on the cooling surfaces is impacted significantly, which consequently may result in non-uniform freezing results.

This effect may be reduced by applying very low temperature cooling surfaces, but when applying very low cooling surface temperatures, e. g. below about −60° C., the receptacles may start suffering or even breaking in the freezing process.

Alternatively, instead of pre-cooling the cooling surfaces, the batch of receptacles may be arranged on non pre-cooled cooling surfaces, which are then gradually cooled to the desired temperature. However, gradually cooling the receptacles results in freezing products of another quality, for example because the freezing process is influenced by convection and supercooling effects in the aqueous solutions, which results often in an amorphous frozen product. Such products would have poor reconstitution capabilities after freeze-drying.

It is also possible to use shock-freezers to apply shock freezing to the aqueous solutions followed by storing the frozen substances in a cold chamber, e.g. at temperatures of about −45° C. By this way, the frozen substances can be stored for hours or even days, without risking any damage to the product. However, shock freezing typically results in an unpredictable outcome of the freezing process which reflects itself in non-uniform characteristics in the frozen products. Moreover, when applying shock freezing using conventional methods, the cooling effect applied to each of the receptacles varies significantly depending on the position and surrounding of the receptacle inside the batch, which contributes further to the non-uniform characteristics in the frozen products.

The book "Freeze-Drying/Lyophilization of Pharmaceutical and Biological Products, second ed. 2002, Louis Rey, Joan C. May, page 247" describes how in the conventional approach the first stage of freeze-drying involves freezing the solution to remove solvent (typ. water) from the drug and excipients through the formation of ice. The resulting semi-frozen system is cooled further to transform all components into a frozen state. A selected time/temperature profile is achieved by placing the solution, which is commonly held in glass vials or syringes or the like, onto cooled shelves.

Suspended impurities in the solution or imperfections in the walls of the container initiate heterogeneous nucleation during freezing. This event almost always involves supercooling whereupon crystallization occurs below the equilibrium freezing point of the solution.

Consequently, when freezing does occur, crystal growth tends to be rapid and results in a complex mixture of crystalline, amorphous and metastable materials. In other words, during freezing, the thermal gradient within the solution is determined implicitly by the temperature of the chamber or cooled shelves, the type of receptacle used and the thermal conductivities of the materials within the solution, and is not explicitly controllable. Moreover, during the freezing process, convection effects induce material flow in the solution, which results in an even less uniform freezing environment within the solution.

In the prior art, this problem is related to as supercooling and heterogeneous nucleation, i.e. the sudden transformation from the aqueous solution to an irregular mixture of crystalline, amorphous and metastable materials, and is known to be difficult to solve. In this respect, there are for example suggestions to add salt or organic solvents to the aqueous solution, in order to influence the structure and size of the resulting ice crystals.

Alternatively, and as applied in accordance with the present invention, the negative effect of supercooling can be avoided by constraining the freezing process to take place at the melting point (equilibrium freezing point), whereby the freezing at the melting point gradually shifts the freezing front throughout the material, and therewith automatically assures constant and uniform freezing conditions throughout the freezing process. Due to the uniform freezing conditions, and the relatively slow propagation speed of the freezing front throughout the material, the freezing process taking place at the melting point is characterized by high molecular mobility and sufficient settling time for allowing the molecules to optimally arrange themselves, i.e. in line with the ice crystal structure.

The document "The Importance of Freezing on Lyophilization Cycle Development" Patapoff et al., BioPharm, March 2002, P. 16-21 discusses how directional freezing can be used to obtain straight, vertical channels in the frozen substance. For this purpose, solutions in receptacles are pre-cooled, nucleated at the bottom of the receptacle with dry-ice, and frozen in a freezing process on a $-50°$ C. shelf, ice crystals propagate vertically and generate channels in the frozen substance, which is advantageous when water vapor needs to be drawn from the material during sublimation. It follows, for example, that the vertical freezing results in a higher sublimation rate and lower product temperature during primary drying.

Surprisingly it has been found that one of the main factors controlling growth of these channels is the temperature gradient between the bottom of the receptacle immersed in refrigerant on a conductive plate, and the medium surrounding the upper surface of the material. The temperature gradient is the driving force for ice crystal growth, and causes the ice crystals to form in a direction parallel to the heat flow, and perpendicular to the cooling surface.

On one hand a sufficiently low temperature of the conducting plate induces a stable temperature gradient for primary and secondary nucleation and driving the ice crystal growth at the melting point, while an insufficiently low temperature of the conductive plate, before primary and secondary nucleation can take place, could allow convection currents in the solution to weaken the temperature gradient, i.e. change the way of freezing and disturb and deteriorate the crystal growth at the gradually shifting melting front. However, on the other hand when very low temperatures are applied by the conductive plate, the material of the receptacle containing the liquid substance was assumed to suffer because of the low temperature applied during the complete freezing process. Consequently, having very low temperature applied during the complete freezing process may damage or even break the receptacle and thereby render the frozen sample unusable.

As to the prior art, reference is made also to J A Searles, J F Carpenter, T W Randolph; Journal of Pharmaceutical Sciences Vol 90, No. 7, July 2011, cf. page 861.

U.S. Pat. No. 4,531,373 refers to the difficulty to achieve the optimal cooling rate in directional cooling of cells, which minimizes both problems associated with cooling too slowly and the mechanical glass transition damage associated with cooling too fast. In U.S. Pat. No. 4,531,373 the focus is on the careful cooling/freezing living cells which later on can be defrosted without losing their viability.

There is thus a need for, and it would be advantageous to have to be performed on an industrial scale, a method and apparatus for directional freezing or freeze-drying of a liquid substance and providing a frozen product with improved uniformity while reducing the risk of thermally breaking or damaging the receptacles containing the liquid substances to be frozen. In the case of freeze-drying, it would also be advantageous to have the crystal structure of the frozen products construed to support the sublimation in the drying process and to reduce the reconstitution time of the freeze-dryed products (e.g. of precious pharmaceutical products).

SUMMARY

These problems are solved according to the present invention by providing a method and apparatus for the directional freezing of liquid substances, e.g. aqueous solutions, contained in at least one receptacle, and a method and an apparatus for freeze-drying by the use of directional freezing.

By the use of the method and apparatus according to the present invention, the aqueous solutions undergo so called primary and secondary nucleation in the course of forming the seed or zone of nucleation and are frozen subsequently in a directed manner at the melting point/equilibrium freezing point to circumvent convection and supercooling effects from influencing the freezing process. Consequently, the freezing process generates a porous ice crystal structure which supports the sublimation of the frozen product during its drying in the freeze-dryer sublimation process. Moreover, a two-step freezing approach is preferably applied to reduce the risk of thermally breaking or damaging the receptacles. These and other advantages related to the present invention are discussed in more detail below.

According to a first aspect of the present invention, a freezing apparatus for freezing a liquid substance contained in at least one receptacle is provided, wherein a cooling surface comprised by the freezing apparatus and having a temperature less $-130°$ C. (143.15 K) is adapted to make direct or indirect surface contact with the receptacle and thereby to have a portion of the liquid substance, which is contained in the receptacle in proximity of the cooling surface, form a seed or initial zone of nucleation.

In an embodiment according to the use of the method and apparatus according to the present invention the temperature of the liquid substance when filled in the receptacles and supplied to the cooling surface has a temperature of $4°$ C. to $28°$ C., in a further embodiment of $10°$ C. to $25°$ C. and a further embodiment of 15° C. to 25° C. Thus, the receptacles with the liquid substance therein may have room temperature when being placed on the extremely cold cooling surface.

After forming the seed or zone of initial nucleation and before the liquid substance contained in the receptacle has been completely frozen, the freezing of the liquid substance remaining in the receptacle is preferably completed by directional ice crystal growth in a different cooling environment, which is less likely to overstress the material of the receptacle, for example due to thermal contraction of the frozen substance contained in the receptacle.

Herein, the surface contact between the receptacle and the cooling surface is preferably direct, wherein an indirect surface contact might be made when there a heat conducting material is arranged between the receptacle and cooling surface. The heat conducting material could for example represent the bottom plate of a tray standing on the cooling surface, wherein the receptacle is arranged to stand inside the tray. The apparatus according to the invention comprises a transport means adapted to move the receptacle away from the cooling surface to a region of a cooling chamber comprised by the apparatus, when said portion of the liquid substance has formed the seed or zone of nucleation or initial solidification inside the receptacle. The cooling chamber is adapted to receive and cool the receptacle, so that the liquid substance remaining in the receptacle is frozen by continuing crystal growth. The cooling chamber may for example have a cooling agent sprayed into the chamber, or for example have cooling elements or any other conventional cooling means that cool the air inside the chamber. It follows that the liquid substance remaining in the receptacle may be frozen in the cooling chamber, without having the receptacle touch the cooling surface. The ambient temperature of the receptacle in the cooling chamber is in the range of −60° C. to −5° C. (213.15 K-268.15 K), preferably −55° C. to −25° C.

Preferably, the apparatus further comprises a tunnel or casing arranged between the cooling surface and the cooling chamber, so that when the receptacle is moved away from the cooling surface to a region of the cooling chamber, the tunnel or casing isolates the receptacle from the environment, e.g. to avoid the condensation of water vapor. Here, in order to prevent water vapor from entering the tunnel or casing, the apparatus preferably further comprises means for inducing overpressure inside the tunnel or casing, e.g. by adding N2 gas.

According to the first aspect of the present invention, the cooling surface may be arranged outside the cooling chamber and the transport means adapted to move the receptacle away from the cooling surface into the cooling chamber.

Alternatively, the cooling surface may be arranged inside the cooling chamber and the transport means adapted to move inside the cooling chamber the receptacle away from the cooling surface to said region of the cooling chamber, for example by arranging the cooling surface close to the entrance, e.g. door or pass-through hatch, of the cooling chamber. In this case, the cooling surface may contribute to or carry out the cooling of the air inside the cooling chamber. Also in this case, because the transport means is adapted to move inside the cooling chamber, the transport means may have smaller dimensions than when the cooling surface is arranged outside the cooling chamber.

In any case, the transport means may be selected from the group of: a conveyor, such as a band or belt conveyor, a robot arm and a lifting device, depending on the relative arrangement between the cooling surface and the respective region of the cooling chamber.

According to the first aspect of the present invention, the transport means may comprise a frame, a rack or a grid receiving a plurality of said receptacles, wherein the receptacles are arranged inside the frame or in openings or holes of the grid or rack. The frame is preferably selected when the bottom shape of the receptacles allows them to stand freely on the cooling surface, while the rack or grid are usually more suitable for supporting receptacles having a round or uneven bottom surface, which prevents the receptacles from standing freely on the cooling surface. The above types of transport means are advantageous when a plurality of receptacles containing the liquid substance are to be frozen, i.e. a block or a set of receptacles, and are preferably moved simultaneously, rather than requiring each individual receptacle to be moved independently by the transport means. It is further preferred that the grid or rack is adapted to suspend the receptacles by holding and aligning the receptacles at their upper ends, in particularly when the receptacles have a round or uneven bottom surface, which prevents the receptacles from standing freely on the cooling surface. Consequently, the lower parts of the receptacles suspend downwardly from the grid or rack, which for example reduces the risk of not providing a proper thermal conductivity between the receptacles and cooling surface, when the receptacles received by the grid or rack are arranged to stand on the cooling surface.

According to the present invention, the region of the cooling chamber, wherein the liquid substance remaining in the receptacle is frozen, has a temperature which is higher than the temperature of the cooling surface. Such a temperature difference between the cooling surface and the cooling chamber contributes to reducing the risk of damaging the receptacle due to thermal effects when the liquid substance remaining in the receptacle is being frozen in the cooling chamber. The temperature of the respective region of the cooling chamber, in which the liquid substance remaining in the receptacle is frozen, is in the range between −60° C. and −5° C. (213.15 K and 268.15 K) and more preferably at −45° C. (228.15 K). In this respect, the temperature of the respective region of the cooling chamber refers to an air temperature measured inside the cooling chamber, for example in the center of or close to a wall or edge of the cooling chamber. Alternatively, the respective temperature of the cooling chamber may refer to an average temperature inside the cooling chamber, which may for example be calculated by averaging a plurality of air temperature measurements taken by temperature sensors at different locations inside the cooling chamber, and may thereby estimate the temperature of the region of the cooling chamber where the liquid substance remaining in the receptacle is frozen.

According to the present invention, the cooling surface has a temperature lower than −130° C. (143.15 K), preferably in the range of −170° C. to −196° C. (103.15 K-77.15 K). Measurements and tests have shown that by applying cooling surface temperatures in these ranges, the seed or zone of nucleation or initial solidification can be generated very quickly and, if desired, maybe delimited to a relatively small volume such that the remaining large proportion of the liquid substance in the receptacle may be subjected to be frozen in the cooling chamber, thus avoiding supercooling and a more uniform freezing process may take place in the receptacles, which adds to the uniformity of the resulting products contained in the batch.

On the other hand and according to a different mode of operation, the receptacles still remain on the extremely cold cooling surface until the substance is almost completely frozen or definitely completely frozen within the respective receptacles. It should be made sure that the temperature of the formed ice within the receptacle during the directional freezing process does not fall below −70° C. (203.15K), preferably not below −50° C. (223.15K), in order to ensure that the ice remains sufficiently weak during the freezing process such that the risk of damaging the receptacles is eliminated or at least considerably minimized.

It was not foreseeable that the extremely low temperatures of the cooling surface could be applied to the receptacles in an industrial scale process without remarkable increasing the risk of damaging the receptacles which are preferably made of glass and being preferably standard vials, laboratory bottles, syringes or the like.

The initial fast cooling of a portion of the substance in the receptacle with extremely low temperature prevents liquid substances contained in the receptacle to circulate due to convection induced in the fluid, which could weaken the temperature gradient effect of applying directional freezing and consequently could deteriorate the uniformity of the resulting products.

According to the present invention, the cooling surface may for example be horizontally flat and adapted to make direct or indirect surface contact with the receptacle by having the receptacle stand on the cooling surface or a heat conducting material arranged between the receptacle and cooling surface. Here, the receptacle may for example have a flat or a round outer bottom surface, or a bottom surface defining a circular contact area with the cooling surface or the heat conducting material arranged between the receptacle and cooling surface. The round outer bottom surface of the receptacle may result in a higher concentration of the cooling effect, when cooled when standing e.g. on the cooling surface, and consequently results in a dimensionally smaller seed of crystallization. For this purpose, for example a frame or a rack or a grid may be used to receive and hold the receptacle in the standing position on the cooling surface.

According to the present invention, the cooling surface is preferably a surface of a solid having good thermal conductivity, such as for example the surface of a metal plate or a metal block, further preferred made of aluminum, brass, copper, titan or steel, e.g. stainless steel. The metal block may preferably comprise a hollow space structure, e.g. at least one fluid channel, for guiding a cooling agent to cool the cooling surface to the desired temperature. The cooling agent may for example be liquid nitrogen, alcohol or another cooling liquid.

It should be noted that experiments and tests have shown the effect of applying directional freezing in accordance with the present invention to depend on the volume or volumes of the receptacles used and the amount of fluid substance received by the receptacles. Said at least one receptacle can be in an embodiment according to the present invention a flask and/or a vial. Further, according to the present invention, good results (e.g. product appearance and reconstitution behavior/time) have been obtained by having the at least one receptacle, receiving the fluid substance to be frozen, made of glass or plastic. In an embodiment according to the present invention a receptacle volume in the range of 1.0 ml to 100 ml is used, in a further embodiment of 1.5 to 40 ml and in an even further embodiment of 1.5 ml, 5 ml, 7 ml or 35 ml is used. Preferably, the filling volume of the receptacles, i.e. the part of the capacity of the receptacles that is being occupied by the liquid to be frozen, is in the range of 10%-70%, particularly 20%-50%.

According to a second aspect of the present invention, a method of freezing a liquid substance contained in at least one receptacle is provided. The method comprises the step of arranging the receptacle to make surface contact with a cooling surface to cool the receptacle and thereby to have a portion of the liquid substance, which is contained in the receptacle in proximity of the cooling surface, form a seed or zone of nucleation or initial solidification. Herein, the surface contact between the receptacle and cooling surface may be direct or indirect, wherein an indirect surface contact is made when there a heat conducting material is arranged between the receptacle and cooling surface. The heat conducting material could for example represent the bottom plate of a tray standing on the cooling surface, wherein the receptacle is arranged to stand inside the tray.

According to some embodiments, the step of continuing the freezing procedure is performed such that after forming the seed or zone of nucleation or initial solidification and before the liquid substance contained in the receptacle has been completely frozen, the freezing of the liquid substance remaining in the receptacle is completed by continuing ice crystallization in a different cooling environment, which is less likely to overstress the material of the receptacle, for example due to thermal contraction of the frozen substance contained in the receptacle.

In other words, the method of freezing a liquid according to the second aspect of the present invention may further comprise moving the receptacle away from the cooling surface to a region of a cooling chamber after said portion of the liquid substance has formed a seed or zone of nucleation or initial solidification; and freezing the liquid substance remaining in the receptacle in the cooling chamber.

It is also possible in the scope of the invention to transfer the receptacle from the cooling surface to the region of the cooling chamber after ice crystal growth in the receptacle has advanced to a greater extend, e.g. after nearly 30% or 80% or almost 100% of the substance has been solidified by directional freezing. Preferred is a range between 30% and 80%.

Preferably, the step of moving the receptacle away from the cooling surface to a region of a cooling chamber may comprise isolating the receptacle from the environment, e.g. to avoid the condensation of water vapor. Here, preferably, the receptacle is moved through a tunnel or casing, and it is further preferred to prevent water vapor from entering the tunnel or casing by inducing overpressure inside the tunnel or casing, e.g. by adding N2 gas.

The cooling chamber has a temperature which is higher than the temperature of the cooling surface. Such a temperature difference between the cooling surface and the cooling chamber contributes to reducing the risk of damaging the receptacle due to thermal effects when the liquid substance remaining in the receptacle is being frozen in the cooling chamber. It is further preferred that the temperature of the region of the cooling chamber, where the liquid substance remaining in the receptacle is frozen, is in the range between −60° C. and −5° C., further preferred about −45° C. In both respects, the temperature of the respective region of the cooling chamber refers to an air temperature measured inside the cooling chamber, for example in the center of or close to a wall or edge of the cooling chamber. Alternatively, the respective temperature of the cooling chamber may refer to an average temperature inside the cooling chamber, which may for example be calculated by averaging a plurality of air temperature measurements taken by temperature sensors at different locations inside the cooling chamber, and may thereby estimate the temperature of the region of the cooling chamber where the liquid substance remaining in the receptacle is frozen.

According to the second aspect of the present invention, the cooling surface has a temperature in the range of −130° C. to −196° C., preferably in the range of −170° C. to −196° C. Measurements and tests have shown that by applying cooling surface temperatures in these ranges, the task of freezing a portion of the liquid substance to form a seed or zone of nucleation or initial solidification results in an improved uniformity of the ice crystallization and in saving in time for freezing the substance. Applying cooling surface temperatures above −130° C. may result in heterogeneous variants of the frozen product contained in the receptacles which may be a) a directional frozen product, b) a frozen product by supercooling effects at different temperatures or c) a partially directional frozen product and partially frozen product by supercooling effects due to the fact that during the cooling process unfrozen liquid substance contained in the receptacle circulates due to convection currents and/or currents due to gradients of concentration induced in the fluid, which degrades the temperature gradient effect of applying directional cooling and the uniformity of the resulting seed or zone of nucleation or initial solidification.

Experiments and tests have shown that by cooling the receptacle, containing the fluid substance to be frozen, on the cooling surface for about 30 sec to 20 min, preferably at about −196° C., a portion of the liquid substance forms a seed or zone of nucleation as a basis for directional crystal growth in the cooling chamber. For example, a vial of 1.25 ml inner volume filled with 0.3 ml of the substance may be cooled for approx. 30 sec on the cooling surface, whereas a vial of 35 ml inner volume filled with 13 ml liquid substance may be cooled for approx. 20 min on the cooling surface.

According to a third aspect of the present invention, a freeze dryer is provided which comprises the freezing apparatus according to the first aspect of the present invention. The freeze dryer further comprises a condensation chamber having a pressure reducing means or vacuum generator, a cold condenser and means for heating the receptacle containing the substance frozen by the freezing apparatus, so that the frozen substance vapors during sublimation, wherein the condenser is adapted to condense said vapor.

According to a fourth aspect of the present invention, a method of freeze drying a liquid substance contained in at least one receptacle is provided, which comprises the method according to the second aspect of the present invention and the further step of having a condensation chamber comprising a cold condenser and a heater, in order to heat the receptacle containing the frozen substance, whereby the frozen substance is heated to vapor during sublimation and wherein the condenser is adapted to condense said vapor.

Experiments and tests have shown by having the time duration of said sublimation take about 1 to 5 days, further preferred about 2 days, good drying results, were obtained.

It should be noted that by having a liquid substance freeze-dried by using the apparatus for freeze-drying according to the third aspect of the present invention or the method of freeze-drying according to the fourth aspect of the present invention, the resulting freeze-dried substance is obtained by drawing water vapor through the channels made by having the first seed or zone of nucleation or initial solidification grown in the cooling chamber by continued crystallization. As a result, the freeze-dried substance represents a dry porous material, i.e. with empty channels. In this respect, it should be mentioned that the crystal structure of the seed or zone of nucleation formed by freezing on the cooling surface on the one hand, and the ice formed by growing the seed or zone of nucleation or initial solidification in a cooling chamber on the other hand, may differ significantly in characteristics, wherein the first type of ice crystals typically exhibits more amorphous like structures with lower absorption capabilities.

Should it be desired to reverse the freeze-drying by dissolving the freeze-dried material in a fluid, e. g. in water, the empty channels provide fluid channels and additional surface to the freeze-dried material and thereby support the dissolving of the material and the uniformity of the dissolving process. It follows that dissolving a solid material which has been freeze-dried according to the present invention is a more rapid and uniform process in comparison with dissolving solid materials freeze-dried without applying directional freezing.

In summary, it may be noted that the present invention allows to increase the throughput of directional frozen substances on an industrial scale in a directional freezing process while improving the uniformity of the frozen product substance, and it allows to improve lyophilisation based on the directional freezing.

BRIEF DESCRIPTION OF THE FIGURES

In the following, the invention is described by the aid of examples by referring to the attached drawings, in which.

DETAILED DESCRIPTION

Figure 1:
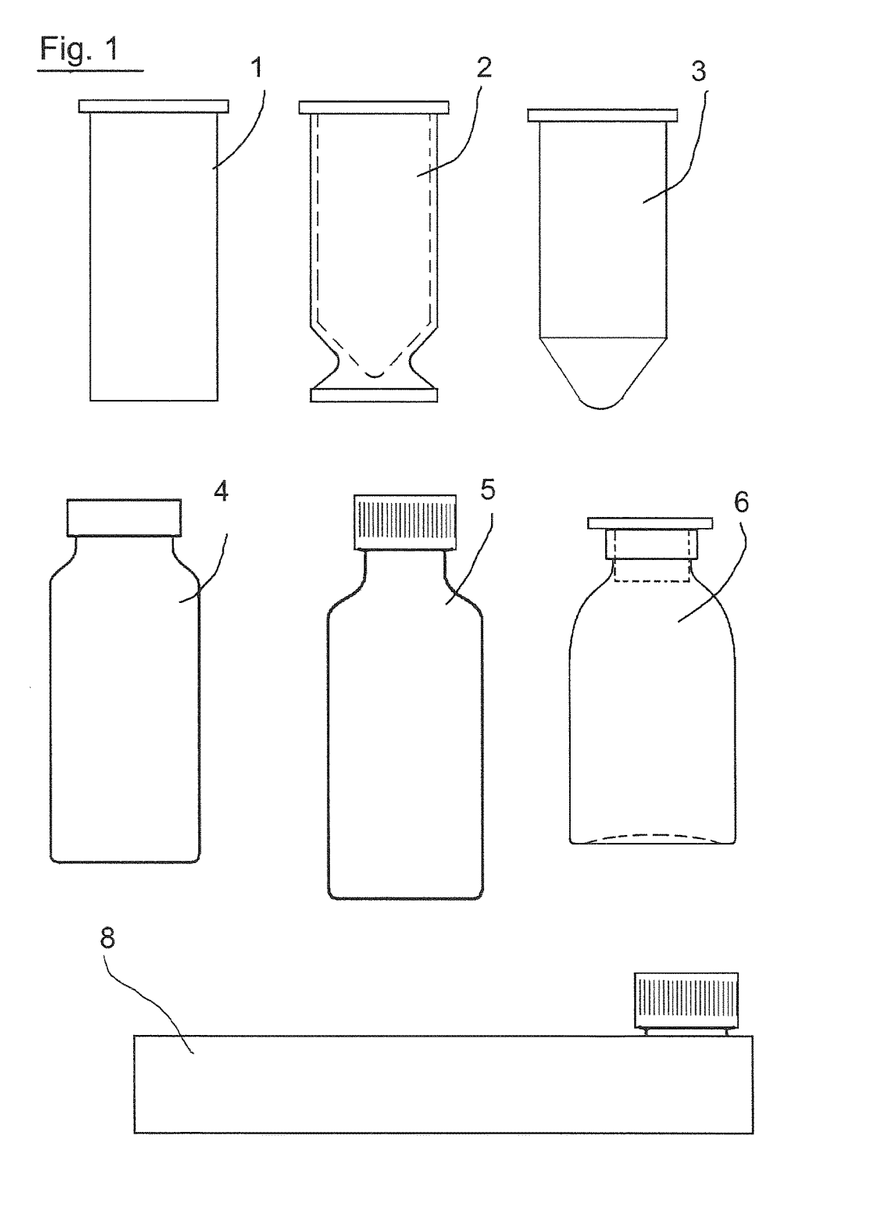
FIG. 1 shows various examples of glass receptacles.

FIG. 1 shows examples of receptacles 1, 2, 3, 4, 5, 6, 8 which may be used in accordance with the present invention. The receptacles shown in FIG. 1 have standard shapes and are preferably made of glass. It should be noted that various other receptacle types can be used as containers for performing the present invention. The receptacles 1-8 in FIG. 1 are shown to have more or less the same size. Actually each of the receptacles 1-8 is available in different sizes with difference volume capacities. For performing the present invention, receptacles with a volume in the range of 1.0 ml to 40 ml have been proven and tested as adequate containers for containing the liquid during the freezing process, but also greater receptacles with volumes up to 100 ml and more are usable as containers for containing the liquid substance during the freezing process. The receptacles may be surface treated, e.g. silanized or siliconized. While the receptacle 3 in FIG. 1 has a conicle rounded bottom surface, the receptacles 1, 2, 4, 5, 8 have flat surfaces and may be arranged to freely stand on a flat cooling surface. The flat bottoms of the receptacles 1, 2, 4, 5, 8 define a circular contact area with the cooling surface. The bottom shape of the receptacle 3 defines a more punctual contact area which may be used to generate a very small seed or initial zone of nucleation by placing the rounded bottom of the receptacle 3 on an extremely cold cooling surface.

The receptacle 8 in FIG. 1 shows a so-called lyoguard container.

The receptacle 6 in FIG. 1 has a concave-shaped bottom that provides a ring-shaped contact area with a cooling surface.

Figure 2:
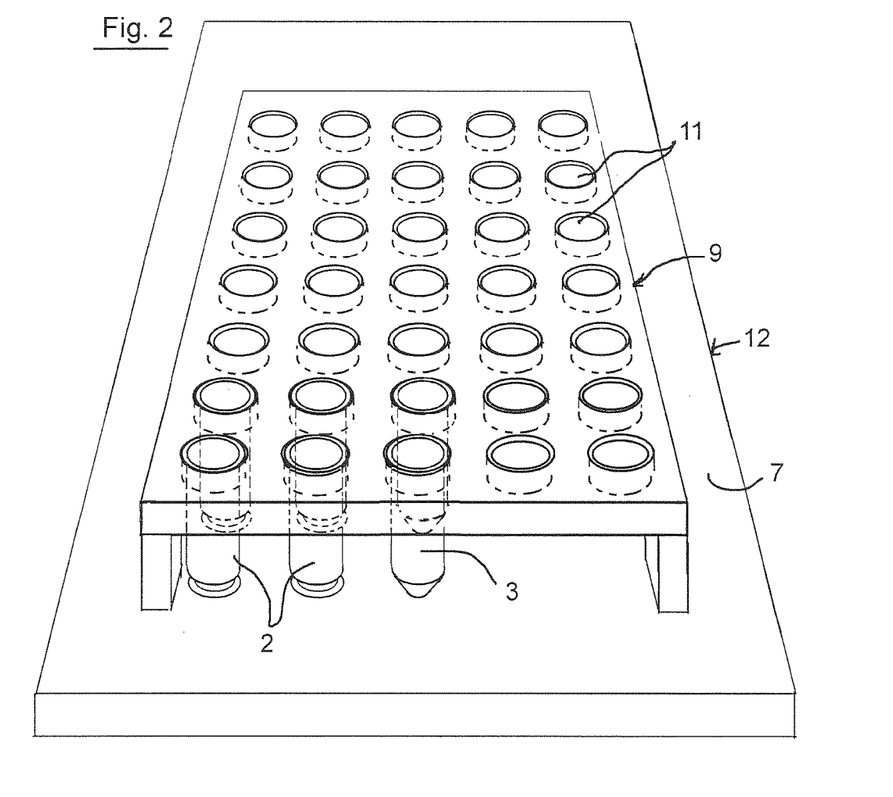
FIG. 2 shows receptacles received in a frame or a grid for transport purposes.

FIG. 2 shows a supporting frame or a rack 9 with a grid-structure containing receptacles 2, 3. The receptacles 2, 3 are arranged in holes 11 of the supporting frame 9, so that the supporting frame 9 supports the receptacles 2, 3 at their upper ends. Consequently, also the receptacles 3 having a round bottom surface may be arranged to stand on a flat cooling surface 7 of the cooling block 12.

Figure 3:
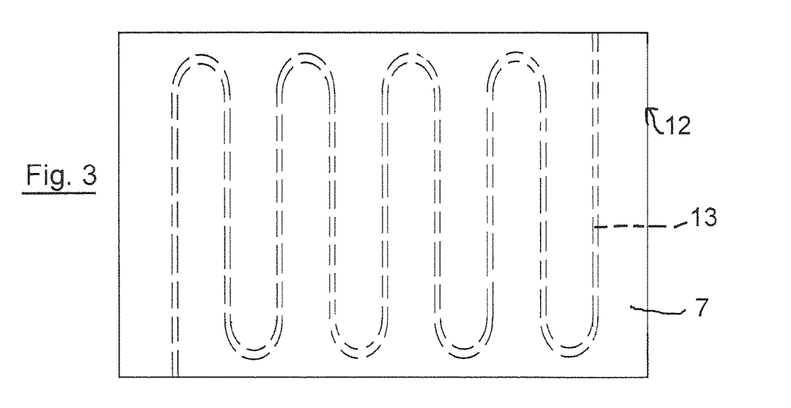
FIG. 3 shows a plan view of a cooling block.

As indicated in FIG. 3, the cooling block 12 has an inner hollow structure in the shape of a wiggly line that constitutes an inner channel 13 through which a coolant agent may be guided. With regard to the present invention, the coolant agent is preferably liquid nitrogen which allows the cooling block 12 to cool down to nearly −196° C. (77.15 K). It is one main feature of the present invention to provide such an extremely cold solid cooling surface 7 and to start a freezing procedure by placing a group of receptacles with the liquid substance to be frozen therein on that cooling surface 7 to make surface contact between the bottoms of the receptacles and the cooling surface 7 but without making a direct contact between the receptacles and the liquid or gaseous coolant agent. Such a course of action is a presumption to perform directional freezing of aqueous solutions on an industrial scale and nevertheless with good uniformity of the freezing product. The invention avoids to deal with open coolant agents such that the coolant agent may be recycled in a circular flow with intermediate conditioning. The closed handling of the coolant agent is also advantageous with regard to health and safety of the operation personnel. A further advantage of using solid cooling surfaces and avoiding direct contact between the receptacles and the coolant agent is the possibility of achieving a very high throughput of directional frozen products. The receptacles may be moved along the cooling surface 7 while maintaining the surface contact therewith in order to provide a continuous process.

In an alternative embodiment, a group or batch of receptacles is placed on the cooling surface 7 to remain there without movement relative to the cooling surface 7 for a predetermined period of time to cool the receptacles and thereby to have a portion of the liquid substance, which is contained in the receptacle in proximity of the cooling surface 7, form a seed or initial zone of nucleation. The contact time between the receptacles and the cooling surface 7 mainly depends on the volume of the liquid substance in each receptacle, on the heat transfer conditions between the cooling surface 7 and the liquid substance near the bottom of the receptacles, and the temperature of the cooling surface 7.

The liquid substance may be an aqueous solution of at least one chemical reagent, particularly a reference reagent, and/or an aqueous solution of biological material, such as a protein or human or animal blood sera, for example. With the general teaching of the present invention, the person skilled in the art will be able to adjust optimum parameters for the dwell time of the receptacles on the cooling surface 7.

The temperature of the cooling surface should be less than −130° C. (143.15 K) and is preferably in a range between −170° C. (103.15 K) and −196° C. (77.15 K). It was not expected that glass receptacles with liquid substances therein could be exposed only with the bottom area on such extremely cold solid cooling surfaces 7 without arising the problem of rupture due to thermal stress of the material of receptacles. In this regard, it should be noted that the receptacles with the liquid substance therein are usually provided at room temperature between 18° C. and 25° C. (291.15 K and 298.15 K) on the cooling surface 7. The inventor has shown that a pre-cooling step of the receptacles before placing them on the cooling surface is unnecessary in almost all cases. In order to provide the seed or initial zone of nucleation on a short time scale it was found that the temperature gradient between the bottom area of the receptacles and the upper regions of the liquid in the receptacles should be relatively great to initiate the forming of a small seed or initial zone of nucleation and to avoid supercooling solidification across a greater region of the liquid in the receptacle.

Figure 4:
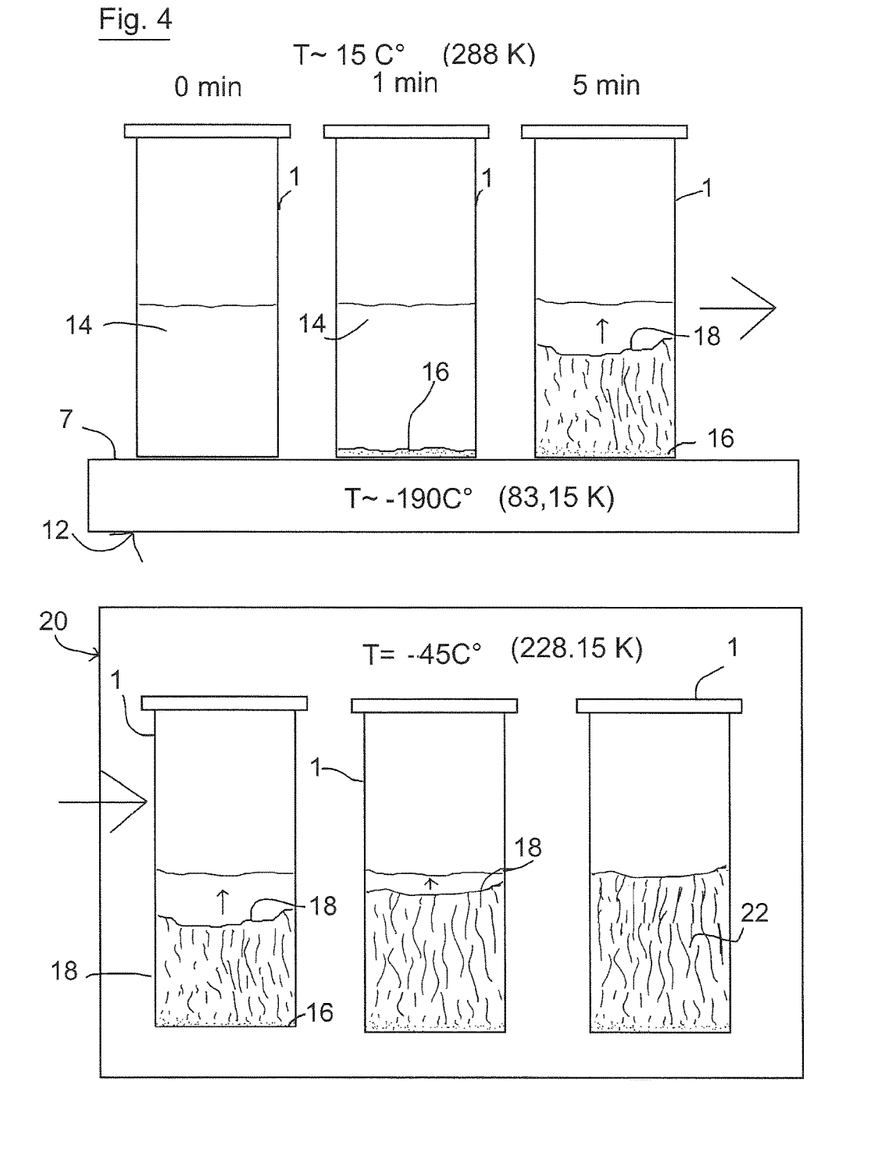
FIG. 4 shows a sequence of steps of a freezing procedure in the course of directional freezing according to the present invention.

In FIG. 4, there is shown an example of a sequence of steps of the freezing procedure. The upper part of FIG. 4 shows a receptacle 1 freely standing on the cooling surface 7 of the cooling block 12 after dwell times of 0 min, 1 min and 5 min on the cooling surface 7. The ambient temperature above the receptacle may be nearly 15° C., but may be also higher, e.g. 25° C. (289.15 K). The receptacle 1 was placed on the cooling surface 7 with the liquid substance 14 being completely solvent (0 min). After a dwell time of 1 min, a seed or initial zone of nucleation 16 and solidification has been formed on the bottom of the receptacle 1. After this step of forming the seed or initial zone of nucleation 16, the ice front 18 grows vertically from the initial zone of nucleation to the top of the liquid level. The directional freezing causes the ice crystals to propagate vertically and generates approximately vertical channels in the frozen substance. The channels are advantageous when water vapor needs to be drawn from the material during sublimation in a lyophilization process. Therefore, the vertical freezing results in a higher sublimation rate during the primary drying and later on in a faster reconstitution of the final freeze-dried product in the lyophilization process.

However, when performing the experiment by continuing the directional cooling on the extremely cold cooling surface 7 until the liquid substance contained in the receptacle 1 has been completely frozen and the substance has reached a temperature of <−70° C. in the complete reagent volume, it becomes evident that the receptacles need to cope with a high mechanical strain, in particular in the latter stage of the freezing.

Experiments have shown that in at least a portion of the receptacles made of glass, which undergo such a cooling process, the formed ice starts to make cracking noises and even to crack due to the mechanical strain induced by the contraction of the ice in the latter stage of the freezing process. Further, the mechanical strain induced in the ice also impacts the receptacles made of glass, and consequently only a portion, e.g. less than between 90%-99% of the receptacles survive the complete process of directional freezing on the cooling surface 7, i.e. freezing until the liquid substance contained in the receptacles has been completely frozen on the extremely cold cooling surface 7. The remaining receptacles, e.g. between 1% and 10% are damaged and fail to provide the frozen material.

It follows in accordance with the present invention, that the time duration of cooling the receptacles on the extremely cold cooling surface 7 is limited, so that when a portion of the liquid substance 14 in the receptacles 1 has formed a seed or initial zone of nucleation 16, and directional crystal growth has been started to a certain extend, the receptacles 1 are moved away from the cooling surface 7. In this example, this is the case when the cooling process in FIG. 4 has reached approximately the stage shown in the situation at 5 min, e.g. for a 35 ml receptacle filled with 13 ml aqueous solution, and is preferably in the range between 1.5 min and 3 min for a 6 ml receptacle filled with 1 ml liquid solution. The dwell time depends on the liquid level in the receptacle and on the size, the geometry and the capacity of the receptacle. As discussed in detail above, if the time duration of freezing on the cooling surface 7 exceeds certain limits, the probability of damaging the receptacles due to contraction of frozen ice becomes significant and represents an undesired effect which should be avoided by limiting the freezing time on the cooling surface 7 according to the present invention.

As shown in the lower part of FIG. 4, the freezing procedure is continued after having the receptacle 1 transported in a cooling chamber 20. The mean temperature in the cooling chamber 20 is set to approx. −45° C. (228.15 K), and this is the ambient temperature of the receptacle in the cooling chamber 20. The freezing procedure is continued in the cooling chamber 20 to completely freeze the substance 14 such that starting from the initial zone of nucleation 16 and an initial layer of directionally frozen substance, directional freezing of the liquid substances with a propagating crystallization front 18 occurs at or near melting point temperature of the substance at the crystallization front 18. Finally, the receptacle 1 contains a completely frozen block 22 of the substance 14 with directional grown ice crystals defining approximately vertically extending channels of microscopic size. The receptacles 1 with the completely frozen substance therein may be stored in the cooling chamber.

It is to be noted that in certain modes of operation the receptacle remains on the cooling surface 7 until the completely frozen block 22 has been formed, wherein it is preferred to make sure that the temperature of the formed ice does not fall below −70° C. Thereafter the receptacle with the frozen substance therein may be stored in the cooling chamber.

It is important to ensure that the seed or initial zone of nucleation 16 does not completely melt before the respective receptacle 1 has been transported into the cooling chamber 20. In this respect, the thermal environmental conditions of the receptacle during its transport from the cooling surface 7 to the cooling chamber 20 represent conditions which should be accounted for when an acceptable lower limit of freezing time on the cooling surface 7 is determined. For example, the receptacle is typically moved in a batch of receptacles from the cooling surface 7 to the cooling chamber 20 inside a tray, wherein the tray may have room temperature or be pre-cooled for reducing the melting vulnerability. The transport time required to transport the receptacle from the cooling surface 7 to the cooling chamber 20 can play a significant role also, depending on the air temperature of the environment used for transporting the receptacle. Other factors are for example related to the thermal conductivity between the receptacle and its environment, e.g. via the thermally conducting trays used for the receptacles transportation, and, as mentioned above, may be related to the size and a type of the receptacle. Moreover, the amount of liquid solution remaining in the receptacle, after freezing on the cooling surface 7, may convey heat to the initial zone of nucleation and thereby contribute to the undesired melting effect.

Experiments have shown that by using −20° C. pre-cooled transport trays for transporting the receptacles from the nearly −196° C. (77.15 K) cold cooling surface 7 to the cooling chamber 20, wherein the transport time is about 2 min at room temperature, and wherein the cooling chamber temperature is about −20° C. (253.15 K), the criteria described above result in the following suitable freezing times on the cooling surface: about 6-16 min for 35 ml receptacles containing 13 ml of BSA (Bovine Serum Albumin), about 3-5.5 min for 5 ml receptacles containing 2.2 ml BSA, and about 1.5-3 min for 5 ml receptacles containing 1.1 ml BSA.

Similar experiments have shown that by using transport trays having room temperature for the transporting the receptacle from the nearly −196° C. cold cooling surface 7 to the cooling chamber 20, wherein the transport time is about 2 min, and wherein the cooling chamber temperature is about −20° C., the criteria described above result in the following suitable freezing times on the cooling surface: about 6-10 min for 35 ml receptacles containing 13 ml of BSA, about 3-5.5 min for 5 ml receptacles containing 2.2 ml BSA, and about 3 min for 5 ml receptacles containing 1.1 ml BSA.

Figure 5:
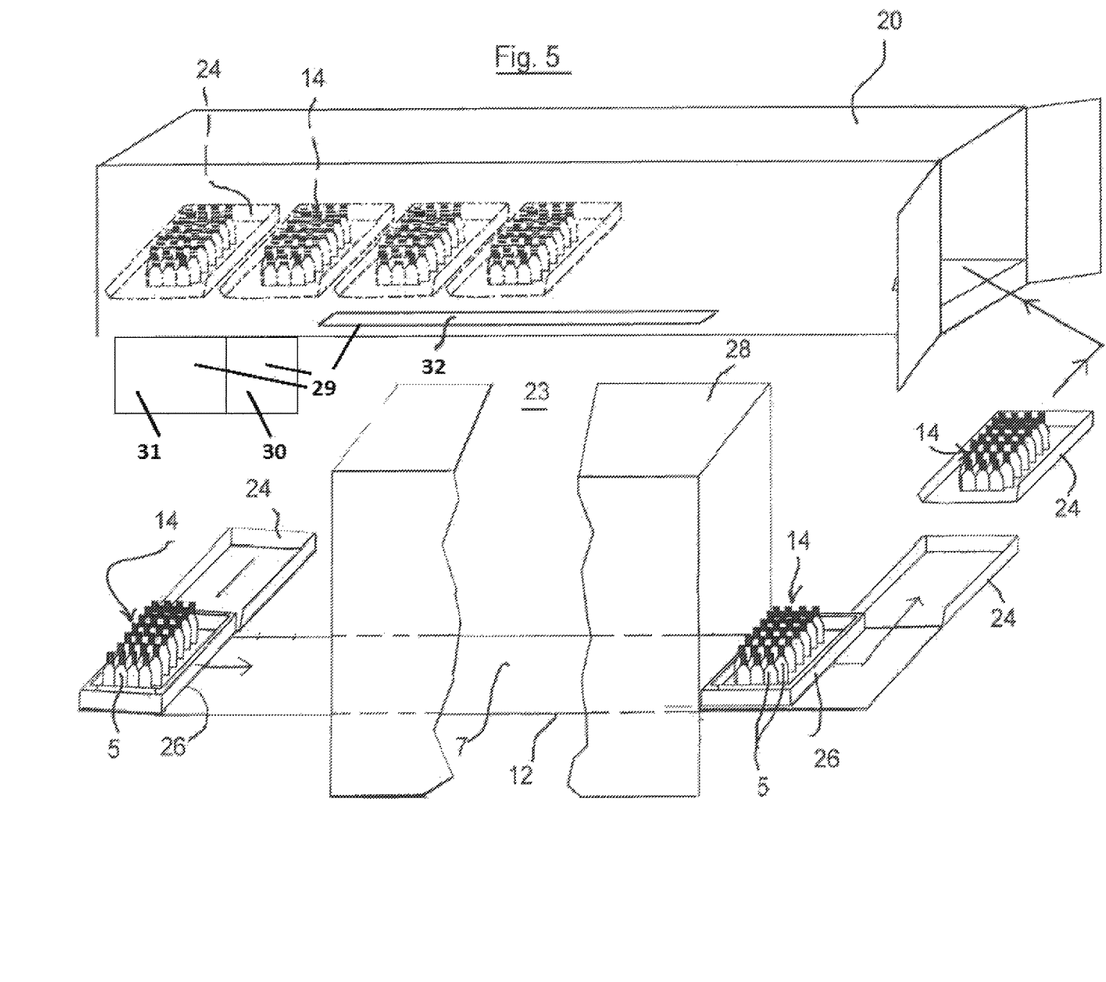
FIG. 5 shows in a schematic perspective view an apparatus for the freezing of liquid substances according to the present invention.

FIG. 5 shows an embodiment of an apparatus 23 according to the present invention in a schematic view.

A batch 14 of receptacles 5 filled with an aqueous solution as a liquid substance is delivered on a tray 24 to the apparatus 23. Frame 26 is used to sidewardly enclose the batch 14 of receptacles 5 on that tray 24 and to draw the batch away from the tray 24 onto the cooling surface 7 of the cooling block 12 as shown in the lower left part of FIG. 5. The receptacles 5 are arranged to freely stand with their bottoms on the cooling surface 7 with the frame 26 remains as a fencing of the batch and as an auxiliary transport means. The frame 26 is moved along the cooling surface 7 through a tunnel 28 with the bottoms of the receptacles 5 in contact with the cooling surface 7, the temperature of which is nearly −196° C. (77.15 K). The tunnel 28 isolates the receptacles 5 from the outer environment, e.g. to avoid condensation of water vapor. In order to prevent water vapor from entering the tunnel 28, the apparatus may comprise means for inducing overpressure inside the tunnel 28, e.g. by injecting gaseous nitrogen at approx. room temperature to hold off air moisture. The frame 26 may be automatically moved along the cooling surface 7 with a pre-determined speed such that the dwell time of the batch 14 of receptacles 5 is sufficient long to allow the liquid substance to form a seed or initial zone of nucleation 16. After the batch 14 of receptacles 5 has left the tunnel 28, the batch 14 of receptacles 5 is moved on a waiting tray 24 (left lower part of FIG. 5) by moving the frame 26 from the cooling surface 7 onto the tray 24. The frame 26 can be removed from the tray 24 leaving the batch 14 of receptacles 5 on the tray 24. The tray 24 with the batch 14 of receptacles 5 thereon is then transported to the cooling chamber 20. The cooling chamber 20 can be combined with the condensation chamber of a freeze-dryer for performing lyophilization of the substance in the receptacles 5.

The transport of the batches 14 of receptacles 5 may be performed manually by an operator, but according to an alternative embodiment of the invention, transport means for automatically moving the receptacles 5 to the cooling surface 7 and further to the cooling chamber 20 are provided. Alternatively, a semi-automatic conveyance system, for example a belt-conveyor or mechanical transporting system, such as a robot device, may be employed.

Figure 6:
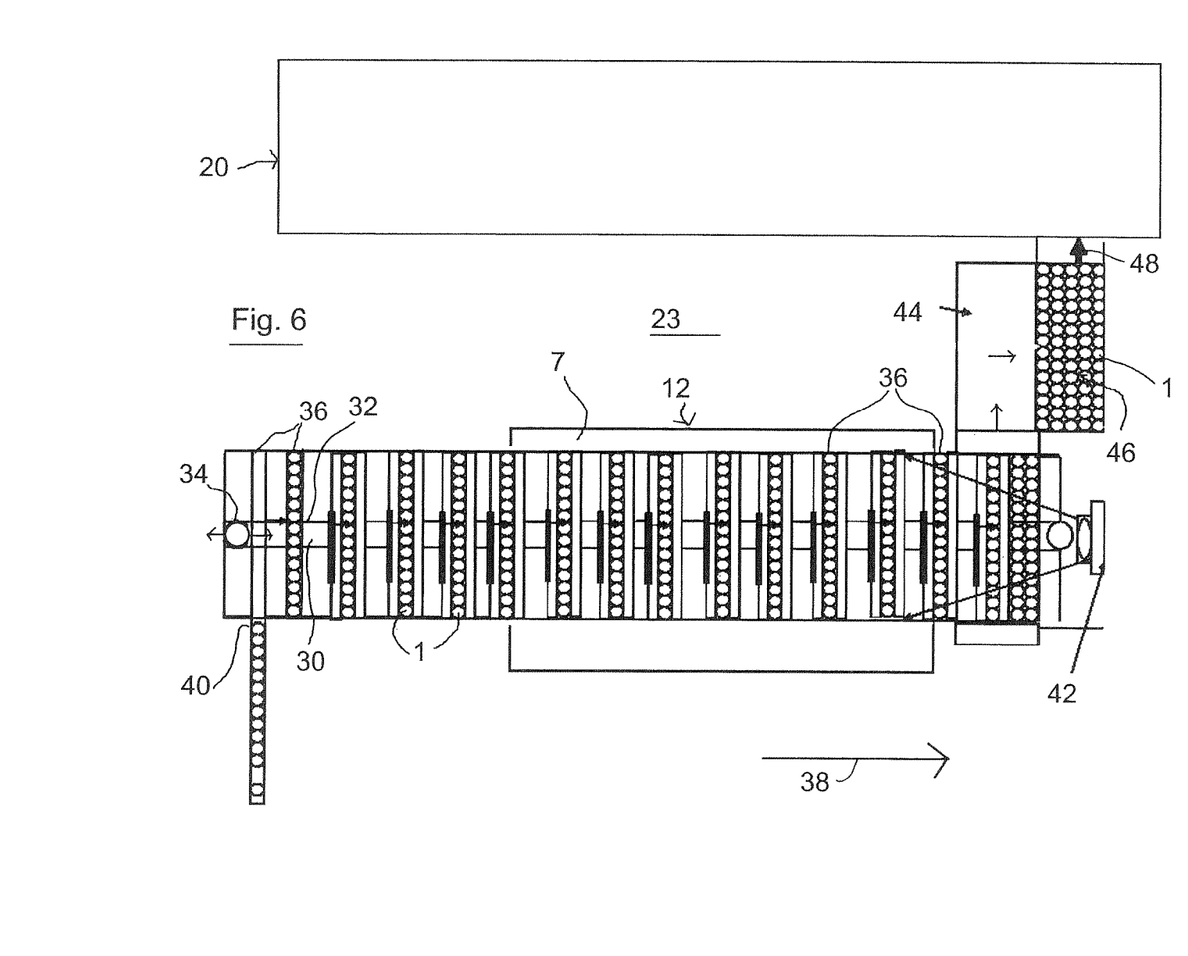
FIG. 6 shows a schematic top view of an apparatus for freezing of liquid substances according to the present invention.

FIG. 6 illustrates a further embodiment of an automated freezing apparatus according to the present invention for performing the method of directional freezing a liquid substance.

The apparatus 23 comprises a belt-conveyor system 30 having a conveyor-belt 32 that is driven by an electric motor 34. The conveyor-belt 32 is adapted to move pockets 36 in the direction of the arrow 38. The pockets 36 are elongated spaces extending transversely with regard to the arrow 38. They have a capacity of receiving e.g. fourteen receptacles 1 in a row. After having been filled with the liquid substance to be frozen, the receptacles 1 are delivered as a batch of fourteen receptacles into respective pockets 36 by means of a row-aligner 40 on the left side in FIG. 6. After having received such a batch of fourteen receptacles 1 in a row, the pocket 36 is moved in the direction of the arrow 38, and a next empty pocket 36 may be aligned with the row-aligner 40 to receive a next batch of receptacles 1. The movement of the pockets 36 with the rows of receptacles 1 received therein is preferably an intermittent stepwise movement under the control of a control means (not shown). During that movement, the receptacles 1 are gliding on flat surfaces to and along the cooling surface 7. In the course of the movement along the cooling surface 7 and during the stops thereon, the receptacles 1 have direct bottom contact with the cooling surface 7 which has a temperature of less than −130° C., e.g. approximately −190° C. (83.15 K).

As explained above, during the contact of the receptacles 1 with such an extremely cold cooling surface 7, a portion of the liquid substance, which is contained in the respective receptacle 1 in proximity of the cooling surface 7, namely adjacent the bottom of the receptacles 1, forms a seed or an initial zone of nucleation. The conveyor-belt 32 moves the receptacles 1 in subsequent steps over the cooling surface 7. Between the steps of conveyor-belt movement, the receptacles 1 are left standing on the cooling surface 7, without moving, for providing an improved thermal contact with the cooling surface 7. The overall-dwell-time of each receptacle on the cooling surface 7 depends on the selected type of receptacle 1 and the filled volume of liquid substance in said receptacle. The timing of the movement of the receptacles is controlled by the control means such that each receptacle 1 has a predetermined dwell time on the cooling surface 7.

According to the embodiment of FIG. 6, the apparatus 23 comprises a camera 42 as a process control means that is oriented to take pictures of each row of receptacles 1 arriving at the right end of the conveying means. The pictures can be analyzed either manually or by an image processing system to monitor the freezing-process of the receptacles 1 containing the liquid substance. The monitoring is used in a further embodiment of the invention to set and adjust the time duration of freezing taking place on the cooling surface 7, e.g. by adjusting the speed of the electric motor 34 accordingly.

According to a further embodiment, a continuous movement of the receptacles along the cooling surface 7 may be performed and the speed of the conveyor-belt 32 is preferably constant and adjusted for the time needed for the freezing process to take place depending on the selected type of receptacle and the filled volume in said receptacle, e.g. approximately 0.6 m/s. At the right most part of the conveying-system in FIG. 6, a defined number of receptacle rows is collected in a frame, grid or tray and pushed block- or batch-wise onto a transfer platform 44 for preparing batches 46 of receptacles 1 to be further transported by automated transport means 48 to the cooling chamber 20.

The transport means 48 may comprise a tray, frame, rack, grid, conveyor-belt or a robot as auxiliary transport means.

The cooling chamber 20 can be a freezer having a plurality of shelves or sliders for receiving the receptacles containing the formed seed or initial zone of nucleation at their bottoms. The cooling chamber 20 may e.g. be equipped with active cooling elements and a ventilator for distributing cold air or coolant gas within the cooling chamber 20.

In the herein discussed examples, the cooling chambers preferably have a temperature close to −45° C. (228.15 K). That temperature is preferably measured using an air temperature sensor mounted at the inner side of one of the cooling chamber walls.

By cooling the receptacles containing the formed seed or zone of initial nucleation in the cooling chamber 20, the freezing process causes the formed seed or zone of initial nucleation to grow until the complete liquid substance has been frozen in the receptacles. In this respect, it should be mentioned that the above explained examples represent one possibility to apply the freezing process in accordance with the present invention. Other possible, but less preferred embodiments of the present invention may e.g. involve a less uniform ice crystal growth, e.g. because the seed or zone of initial nucleation may occupy a larger volume within the receptacle, or because the seed or zone of initial nucleation may due to melting during transport release itself from the walls of the receptacle and initiate ice crystal growth from its position within the receptacle.

As to the explained preferred embodiments of the present invention, the cooling causes ice crystals to propagate vertically and to generate channels in the frozen substance. The channels propagate throughout the interior of the frozen substance, which is for example advantageous when water vapor needs to be drawn from the material during sublimation, i.e. the vertical crystallization growth results in a higher sublimation rate and lower product temperature during the primary drying of a freeze-drying process.

According to the present invention, this advantage is obtained without overstraining the receptacles made of glass. As a matter of fact, experiments and tests have shown that by completing the freezing in the cooling chamber in accordance with the present invention, a significantly lower number of receptacles can be expected to break or get damaged during the cooling process. This result is also achievable according to a special mode of performing the step of continuing the freezing procedure.

Further, the receptacles containing the fully frozen substance can then, e.g. after storage for up to hours or days, e.g. up to 14 days, be moved, e.g. by using the above described trays, to a lyophilizer (condensation chamber) for sublimation, wherein the condensation has a cold condenser, a vacuumizer and means for heating the receptacles under vacuum, so that the frozen substance vapors and the condenser is adapted to condense the vapor. In this example, the time duration for the sublimation is about 2 days, and is usually in the range of 1 to 5 days. Further, after sublimation, the receptacles are typically closed, e.g. by rubber stoppers and/or closures, for preservation purposes.

After the sublimation, the sublimated substance contained in the receptacles has the advantage that channels formed during the vertical, or directional ice growth in the cooling process are still present in the substance. Consequently, by adding a fluid, such as water, to said sublimated substance, the fluid effectively and quickly accesses the material, resulting in a quick and efficient process of dissolving said sublimated substance. Experiments have shown that the sublimated substances generated by conventional methods of controlled or uncontrolled freezing, i.e. supercooling effects, reconstitution of the substance may require up to 30 min for the reconstitution of the material, but only <2 min when the above described approach is applied in accordance with the present invention.

The invention claimed is:

1. A freezing apparatus for freezing a liquid substance contained in at least one receptacle, comprising:
    a cooling device having a cooling surface adapted to receive thereon in surface contact a plurality of receptacles containing a liquid substance to be frozen, and cooling means adapted to cool the cooling surface to a temperature less than −130° C. in order to cool receptacles placed on the cooling surface and thereby to have a portion of the liquid substance, which is contained in the receptacles in proximity of the cooling surface, form a seed or initial zone of nucleation;
    a cooling chamber adapted to receive the receptacles in a cooling region of the cooling chamber and to cool the receptacles received therein to continue freezing of the liquid substances at cooling temperatures in the range between −5° C. and −60° C.; and
    a transport means adapted to transfer receptacles from the cooling surface to said cooling region of the cooling chamber before the liquid substance contained in the receptacles has been completely frozen.

2. The freezing apparatus of claim 1, wherein the cooling surface is arranged outside the cooling chamber and the transport means is adapted to move the receptacle away from the cooling surface into the cooling chamber, or wherein the cooling surface is arranged inside the cooling chamber and the transport means is adapted to move inside the cooling chamber the receptacle away from the cooling surface to said cooling region of the cooling chamber.

3. The freezing apparatus of claim 1, wherein the cooling surface is horizontally flat and adapted to make a direct surface contact with the receptacle by having the receptacle standing directly on the cooling surface.

4. The freezing apparatus of claim 1, wherein the cooling surface is the surface of a metal plate or a metal block wherein the metal block comprises a fluid channel for guiding a cooling agent.

5. The freezing apparatus of claim 1, wherein the transport means comprises a frame, a rack or a grid receiving a plurality of said receptacles, wherein the receptacles are arranged inside the frame or in openings or holes of the grid or rack, and wherein the grid or rack is adapted to suspend the receptacles by holding the receptacles at their upper ends.

6. A freeze dryer for performing the method, comprising the freezing apparatus of claim 1 and further comprising a condensation chamber having a cold condenser and a heater for heating the receptacle containing the substance frozen by the freezing apparatus, so that the frozen substance vaporizes during sublimation, wherein the condenser is adapted to condense said vapor.

7. A method of freezing a liquid substance contained in at least one receptacle comprising the steps of:
    providing the liquid substance in at least one receptacle,
    providing a cooling chamber and a cooling device having a cooling surface;
    setting the temperature of the cooling surface to less than −130° C.;
    starting a freezing procedure by placing the receptacle with the liquid substance therein on the cooling surface to make surface contact between the receptacle and the cooling surface to cool the receptacle and thereby to have a portion of the liquid substance, which is contained in the receptacle in proximity of the cooling surface, form a seed or initial zone of nucleation;
    continuing the freezing procedure to completely freeze the substance such that, starting from the seed or initial zone of nucleation, directional freezing of the liquid substance with a propagating crystallization front occurs at or near melting point temperature of the substance at the crystallization front;
    and transferring the receptacle from the cooling surface to a region of the cooling chamber, with the cooling temperature within said region of the cooling chamber being set to a value in the range between −60° C. and −5° C.,
    wherein the step of transferring the receptacle from the cooling surface to the region of the cooling chamber is performed before the liquid substance contained in the receptacle has been completely frozen.

8. The method of claim 7, wherein containers made of glass are used as receptacles.

9. The method of claim 7, wherein receptacles with volumetric capacities between 1.0 ml and 100 ml are used.

10. The method of claim 7, wherein the liquid substance is an aqueous solution of at least one chemical reagent and/or an aqueous solution of biological material.

11. The method of claim 7, wherein, after having started the freezing procedure, the receptacle is left for a dwell time between 30 s and 20 min on the cooling surface of the cooling device.

12. The method of claim 7, wherein transferring the receptacle from the cooling surface to said region of the cooling chamber is conducted within a time interval less than 5 min.

13. The method of claim 7, wherein transferring the receptacle from the cooling surface to said region of the cooling chamber is conducted in a cooled environment having a temperature less than 5° C.

14. The method of claim 7, wherein a metallic block comprising the cooling surface is provided as a part of the cooling device, said metallic block has an inner hollow space structure through which liquid nitrogen is guided as a coolant.

15. The method of claim 7, wherein the liquid substance in the receptacle, when placing the receptacle on the cooling surface to start the freezing procedure, has a temperature between 15° C. and 28° C.

16. The method of claim 7 further comprising the step of sublimating ice crystals from the frozen substance by heating the receptacle with the frozen substance therein in a condensation chamber at reduced ambient pressure in said condensation chamber.

* * * * *